(12) United States Patent
Gray et al.

(10) Patent No.: US 9,198,805 B2
(45) Date of Patent: Dec. 1, 2015

(54) MENSTRUAL PANT

(71) Applicant: The Procter & Gamble Company, Cincinnati, OH (US)

(72) Inventors: Brian Francis Gray, Cincinnati, OH (US); Brett Darren Seitz, West Chester, OH (US); Andres Ernesto Velarde, Covington, KY (US); Bruce William Lavash, West Chester, OH (US); Guido Bonelli, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 155 days.

(21) Appl. No.: 13/918,476

(22) Filed: Jun. 14, 2013

(65) Prior Publication Data

US 2014/0296814 A1     Oct. 2, 2014

Related U.S. Application Data

(63) Continuation of application No. PCT/US2013/033972, filed on Mar. 27, 2013.

(60) Provisional application No. 61/618,331, filed on Mar. 30, 2012.

(51) Int. Cl.
| | |
|---|---|
| *A61F 13/47* | (2006.01) |
| *A61F 13/472* | (2006.01) |
| *A61F 13/72* | (2006.01) |
| *A61F 13/512* | (2006.01) |
| *A61F 13/511* | (2006.01) |
| *A61F 13/53* | (2006.01) |

(52) U.S. Cl.
CPC ......... *A61F 13/47227* (2013.01); *A61F 13/512* (2013.01); *A61F 13/72* (2013.01); *A61F 2013/51117* (2013.01); *A61F 2013/530802* (2013.01)

(58) Field of Classification Search
CPC ............ A61F 5/44; A61F 13/15; A61F 13/49; A61F 13/56; A61F 13/64; A41B 9/02; A41B 11/02
See application file for complete search history.

(56) References Cited

U.S. PATENT DOCUMENTS

| | | |
|---|---|---|
| 3,929,135 A | 12/1975 | Thompson |
| 4,324,246 A | 4/1982 | Mullane |
| 4,342,314 A | 8/1982 | Radel et al. |
| 4,463,045 A | 7/1984 | Ahr et al. |
| 4,609,518 A | 9/1986 | Curro et al. |
| 4,629,643 A | 12/1986 | Curro et al. |

(Continued)

*Primary Examiner* — Melanie Hand
(74) *Attorney, Agent, or Firm* — Andres E. Velarde

(57) ABSTRACT

A system including a menstrual pant and an absorbent article. The menstrual pant can have a front part; a back part; a crotch part provided so as to bridge between the front part and the back part, the crotch being utilized for fitting a sanitary napkin, a waist opening part provided in an upper edge of the front part and an upper edge of the back part, a pair of leg openings provided below both side edges of the front part and both side edges of the back part; and a lifting strip disposed along the longitudinal centerline in the rear portion. The menstrual pant can apply body-contacting pressures to the wearer's body longitudinally through the crotch of 25 g/cm² to 100 g/cm². The absorbent article can have a topsheet having a body facing surface, a backsheet joined to said topsheet; and an absorbent core disposed between said topsheet. The absorbent article can exhibit a 30-minute Vertical Wicking Height of at least about 12 cm.

21 Claims, 8 Drawing Sheets

(56) References Cited

U.S. PATENT DOCUMENTS

| | | |
|---|---|---|
| 4,950,264 A | 8/1990 | Osborn |
| 4,988,344 A | 1/1991 | Reising et al. |
| 4,988,345 A | 1/1991 | Reising et al. |
| 5,006,394 A | 4/1991 | Baird |
| 5,147,345 A | 9/1992 | Young et al. |
| 5,331,015 A | 7/1994 | DesMarais |
| 5,352,711 A | 10/1994 | DesMarais |
| 5,387,207 A | 2/1995 | Dyer et al. |
| 5,550,167 A | 8/1996 | DesMarais |
| 5,628,097 A | 5/1997 | Benson et al. |
| 5,647,863 A * | 7/1997 | Hammons et al. ............ 604/378 |
| 5,916,661 A | 6/1999 | Benson et al. |
| 6,702,917 B1 | 3/2004 | Venturino |
| 8,083,725 B2 | 12/2011 | Bonelli et al. |
| 2001/0025386 A1* | 10/2001 | Suga et al. ........................ 2/406 |

\* cited by examiner

MENSTRUAL PANT

FIELD OF INVENTION

This application relates to a system including a menstrual pant and an absorbent article.

BACKGROUND OF THE INVENTION

Unlike many types of disposable absorbent articles, absorbent articles such as pads and pantiliners are specifically designed to acquire menstrual fluid. Menstrual fluid differs from other exudates, such as urine, in many important properties, such as viscosity. Therefore, absorbent articles should differ in their structural components from such devices as baby diapers to be optimized for the maximum absorption of menstrual fluid.

For absorbent articles, the fluid insult has very different characteristics in the context of physio-chemical properties (e.g., viscosity, fluid dynamics, etc.) and in the volume and in the time to be absorbed. For example, menstrual flow typically consists of two patterns. One of these is "trickle" flow, which varies from 0.1 to 2 ml per hour. The second pattern is "gush" flow which varies from a few ml in volume delivered over a few seconds. Gush flow can result from an accumulation of menses pooling in the vagina which can then exit the body upon a change in position, such as a transition from sitting to standing. In any event, even with gush flow, the total amount of fluid required to be absorbed into the core in a given time is much less than that required by other absorbent products, such as baby diapers, for example. One practical result is that absorbent articles, rather than needing to be designed to handle gushing fluid, more typically handle fluid through a "blotting" effect.

Desirably, the absorbent article should maintain contact with and conform as closely as possible to the wearer's body. Such a body-conforming capability can increase the effectiveness of the absorbent article by reducing the possibility that menses will travel around the perimeter of the absorbent article and leak. To provide body-conforming characteristics, many menstrual pants increase the forces placed on the body by the menstrual pant such as the waist to hip force and the longitudinal force in the crotch area. These forces, which are higher than a traditional undergarment, can cause discomfort to the wearer.

Accordingly, there is a continuing need for a absorbent article having improved fluid handling such that more menses enter into and remain in the device, and less on the skin and hair of the wearer.

Additionally, there is a continuing need for a absorbent article in combination with a menstrual pant that has improved body fit to better fit the body of the wearer.

SUMMARY OF THE INVENTION

A system comprising menstrual pant and an absorbent article is provided. The menstrual pant has a front part; a back part; a crotch part provided so as to bridge between the front part and the back part, the crotch being utilized for fitting a sanitary napkin, a waist opening part provided in an upper edge of the front part and an upper edge of the back part, a pair of leg openings provided below both side edges of the front part and both side edges of the back part; and a lifting strip disposed along the longitudinal centerline in the rear portion. The menstrual pant applies body-contacting pressures to the wearer's body longitudinally through the crotch of 25 g/cm$^2$ to 100 g/cm$^2$. The absorbent article has a topsheet having a body facing surface, a backsheet joined to said topsheet; and an absorbent core disposed between said topsheet. The absorbent article exhibits a 30-minute Vertical Wicking Height of at least about 12 cm.

Also provided is a menstrual pant. The menstrual pant has a front part; a back part; a crotch part provided so as to bridge between the front part and the back part, the crotch being utilized for fitting a sanitary napkin, a waist opening part provided in an upper edge of the front part and an upper edge of the back part, a pair of leg openings provided below both side edges of the front part and both side edges of the back part; and a lifting strip disposed along the longitudinal centerline in the rear portion. The menstrual pant applies body-contacting pressures to the wearer's body longitudinally through the crotch of 25 g/cm$^2$ to 100 g/cm$^2$.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
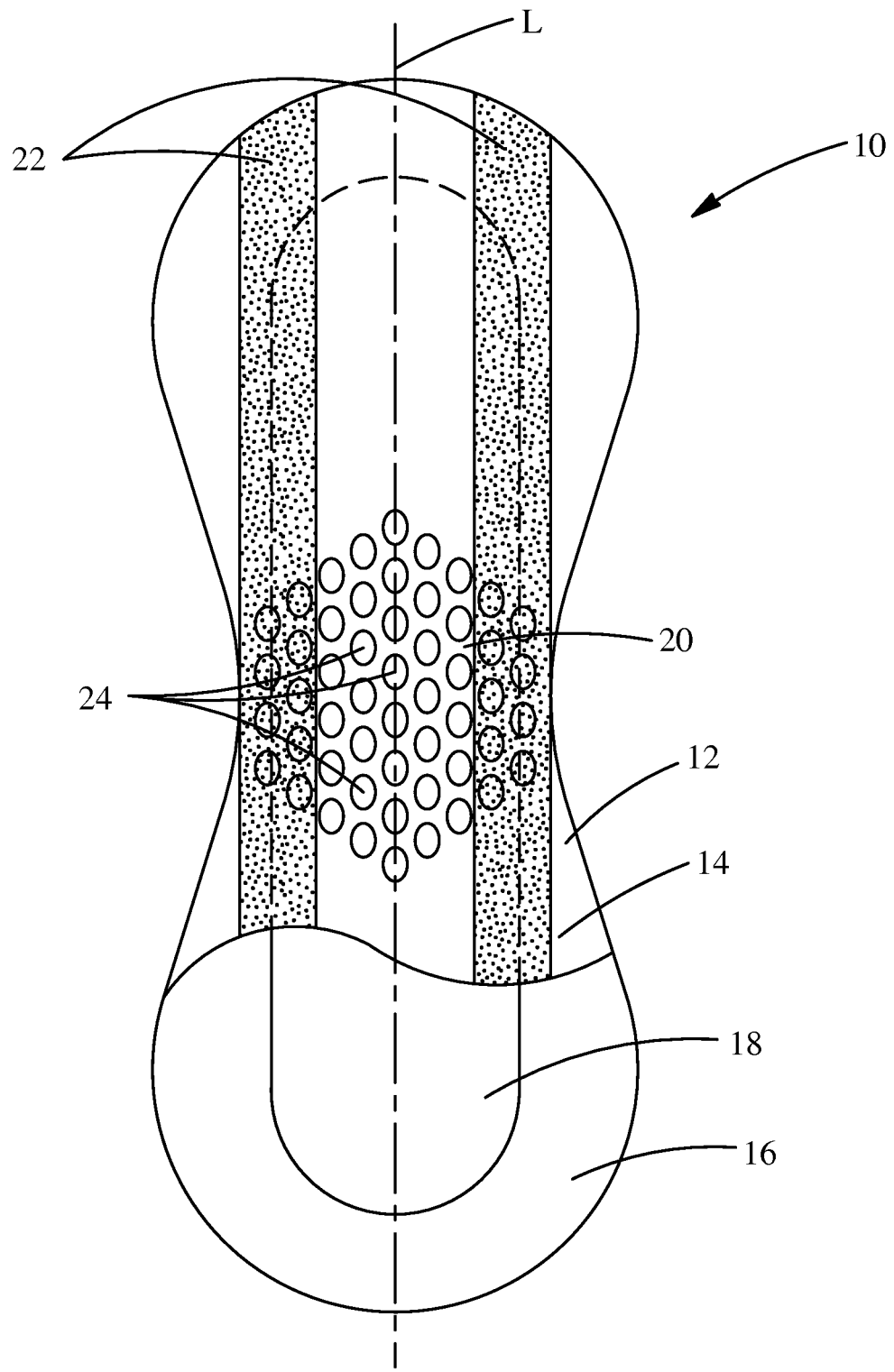
FIG. 1 is a plan view of an absorbent article having an apertured topsheet and a lotion composition.

A system comprising menstrual pant and an absorbent article is provided. The menstrual pant has a front part; a back part; a crotch part provided so as to bridge between the front part and the back part, the crotch being utilized for fitting a sanitary napkin, a waist opening part provided in an upper edge of the front part and an upper edge of the back part, a pair of leg openings provided below both side edges of the front part and both side edges of the back part; and a lifting strip disposed along the longitudinal centerline in the rear portion.

The menstrual pant can apply body-contacting pressures to the wearer's body longitudinally through the crotch of 25 g/cm$^2$ to 100 g/cm$^2$. The absorbent article has a topsheet having a body facing surface, a backsheet joined to said topsheet; and an absorbent core disposed between said topsheet. The absorbent article can exhibit a 30-minute Vertical Wicking Height of at least about 12 cm.

The absorbent article can maintain contact with and covers the inside surfaces of the wearer's labia, the exterior surfaces of the wearer's labia, and covers the menstrual pant or panty. Coverage of all three of these surfaces provides the absorbent article with the greatest opportunity to provide superior leakage protection and to maintain the wearer's body in a clean condition, free of menses. The absorbent article is preferably worn with a menstrual pant or panty that comfortably fits against and conforms to the inside and outside surfaces of the wearer's labia majora. This conforming fit is present regardless of whether the wearer's legs are apart, or together. The menstrual pant or panty preferably maintains a modified cusp-shaped cross-sectional configuration in this area throughout a range of body motions. The absorbent article preferably does not alter or override the tendency of the menstrual pant or panty to achieve this fit. The absorbent article preferably flexes under the forces exerted by the menstrual pant or panty so that it assumes a similar (and preferably the same modified cusp shape) in this region as the menstrual pant or panty.

The absorbent article and menstrual pant or panty preferably function in a manner that can be thought of as being analogous to covering a cut with a bandage. Body fluids are captured at or near their source by using close body contact and comfortable forces to hold the absorbent article in place at the source of bodily fluids. This can be contrasted with using overly-sized sanitary napkin in a loose-fitting pair of panties, which function in a manner that can be analogized to the use of a drop cloth beneath the source of bodily fluids. The absorbent article may cover the wearer's pudendal region, the wearer's perineum, and may extend to cover the wearer's anus. The absorbent article preferably does not extend forward beyond the wearer's mons pubis. This provides a more comfortable, and less noticeable absorbent article since it occludes less of the crotch region of the wearer's body and allows air to circulate around the same. The absorbent article preferably cups the labia from front to back.

As used herein, the term "absorbent articles" refers to articles which absorb and contain body fluids or exudates, and more specifically, refers to articles which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and preferably, to be disposed of in an environmentally compatible manner). Exemplary absorbent articles include disposable feminine hygiene absorbent articles. Such articles include sanitary napkins, interlabial products, and pantiliners. Feminine hygiene articles do not include baby diapers.

As used herein, the term "absorbent core" refers to the component of the absorbent article that is primarily responsible for the liquid handling properties of the article, including acquiring, distributing, and storing body liquids. As such, the absorbent core typically does not include the topsheet or backsheet of the absorbent article.

As used herein, the terms "elastic," "elastomer," and "elastomeric" refer to a material which generally is able to extend to a strain of at least 50% without breaking or rupturing, and is able to recover substantially to its original dimensions, accounting for set, after the deforming force has been removed.

As used herein, the term "menstrual pant or panty" refers to an undergarment designed to be worn with an absorbent article. A menstrual pant or panty may be designed to exert forces on the body in both the waist and crotch regions to conform the pant or panty to the body.

FIG. 1 shows an absorbent article 10, that can be a sanitary napkin or pantiliner, having a body-contacting surface 12 and a topsheet 14 at least a portion 20 of which has a plurality of apertures 24. The absorbent article 10 has a liquid impervious backsheet 16 joined to the topsheet 14, and an absorbent core 18 disposed between the topsheet and backsheet. The sanitary napkin 10 has a longitudinal axis L and may also be provided with additional features commonly found in sanitary napkins, including "wings" or "flaps" (not shown) as is known in the art, and/or a fluid acquisition layer between the topsheet and the absorbent core to promote fluid transport from the topsheet to the absorbent core 18. The topsheet 14 of the absorbent article 10 of the present invention can have a lotion composition 22 disposed onto at least the body-contacting surface 12 thereof.

The terms "body-contacting surface" and "wearer-contacting surface" are used interchangeably herein and refer to one or more surfaces of any article component that is intended to be worn or positioned toward or adjacent the body of the wearer/user for contact between the wearer/user and the article's surface at some time during the use period. The term "garment surface" as used herein refers to the outer or exterior surface of any article component that is intended to be worn or positioned adjacent a wearer's undergarments, or in the case of an absorbent article which is not worn by the user, the garment surface is typically positioned adjacent a user's hand or other implement assisting in the use of the absorbent article. As used herein, the term "wearer" and "user" are used interchangeably as the present invention contemplates absorbent articles which may not be intended to be worn, but rather used to absorb bodily exudates while transferring the lotion compositions of the present invention.

Figure 2:
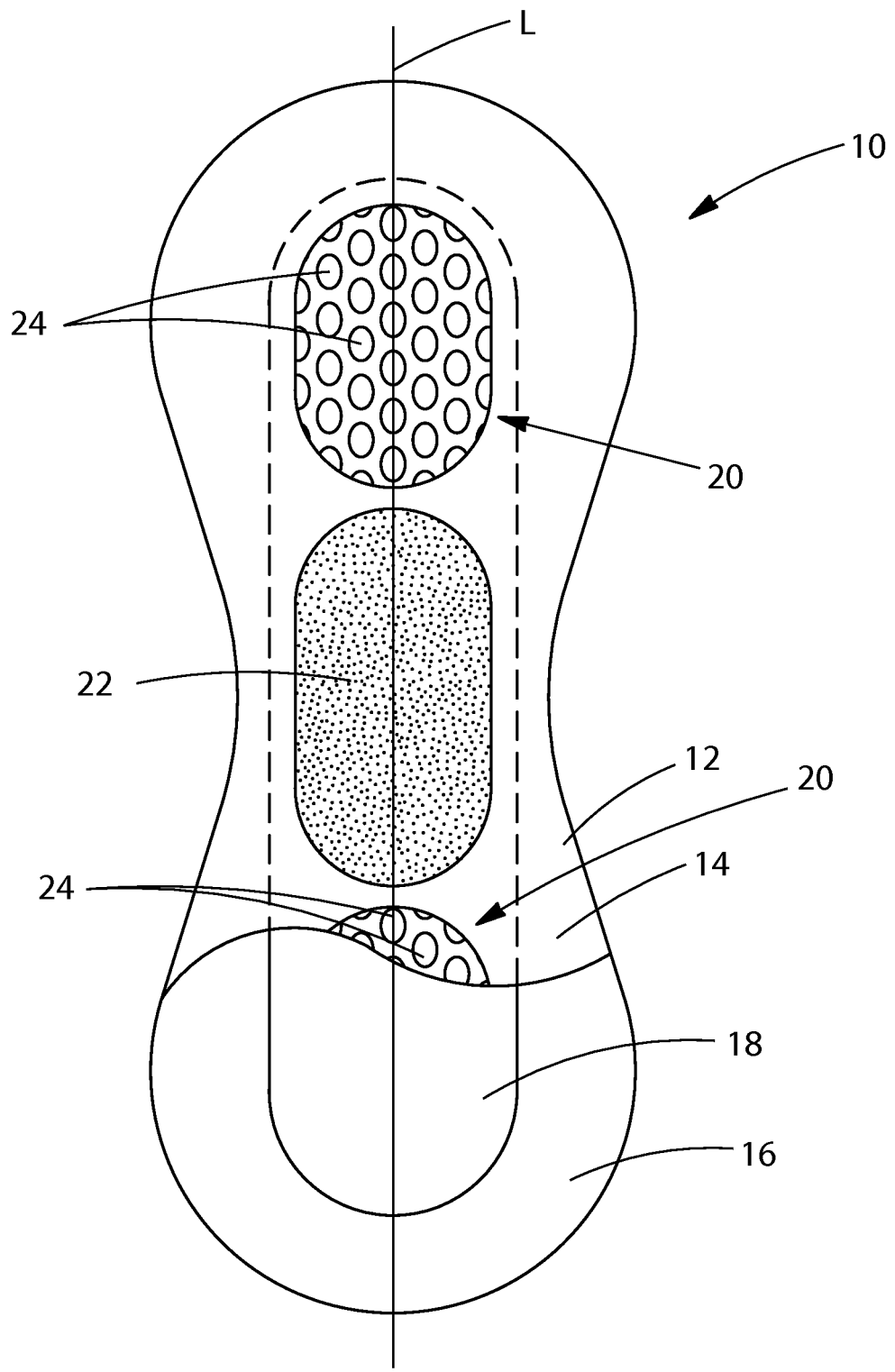
FIG. 2 is a plan view of an absorbent article having an apertured topsheet and a lotion composition.

In FIG. 1 the lotion composition (lotion) 22 is shown as applied in two parallel stripes or bands. Lotion 22 can be applied by means known in the art in any pattern known in the art. For example, lotion 22 can be applied as beads, bands, stripes, and continuous coatings. As shown in FIG. 2, lotion 22 can be applied in a discrete zone such as a centrally-disposed region of the body-contacting surface 12.

The topsheet 14 of the sanitary napkin can include an apertured formed film as is known in the art of sanitary napkins, including Dri-Weave® topsheets used on Always® sanitary napkins. Likewise, the topsheet 14 can be an apertured nonwoven web, for example an apertured nonwoven as disclosed in U.S. Pat. No. 5,628,097 issued May 13, 1997 to Benson et al., or U.S. Pat. No. 5,916,661 issued Jun. 29, 1999 to Benson et al. Topsheet 14 has apertures 24 therethrough on at least a portion 20 thereof to aid in fluid acquisition of viscous menstrual fluid, or sudden gushes of fluid. As shown in FIG. 1, a central portion overlying the absorbent core 18 has a plurality of apertures in a generally oval-shaped pattern. Apertures can be formed by any means known in the art, including by hydroforming (for both film and nonwoven topsheets), hot pin apertureing, slit and stretch, and the like.

The portion 20 of the topsheet 14 comprising a plurality of apertures 24 need not be limited to oval shapes or limited to being in a central portion 20 overlying the absorbent core 18. For example, as shown in FIG. 2, the portion of the topsheet 14 having a plurality of apertures can be disposed off center, nearer one end of absorbent article 10 than the other. Likewise, the plurality of apertures can form a pattern of any shape, including the substantially circular shape shown in FIG. 2.

In general the portion 20 comprising apertures 24 can be identified by the density of apertures that make up the portion 20. For example, apertures can be in relatively closely-spaced rows of closely-spaced apertures to form a region or zone of apertures as shown in FIGS. 1 and 2. Likewise, there may be more than one portion 20, i.e., more than one region or zone, of apertures 24 in topsheet 14.

The topsheet 14 may be a 30 gsm hydrophobic bicomponent fibrous nonwoven purchased from Pegas and apertured according to the process as disclosed in U.S. Pat. No. 5,628,097 issued May 13, 1997 to Benson et al., or U.S. Pat. No. 5,916,661 issued Jun. 29, 1999 to Benson et al. The topsheet may contain hydrophilic fibers, hydrophobic fibers, or combinations thereof. Apertures 24 may be on average 2.3 mm2 in area and the portion 20 comprising apertures 24 may have an average percent open area of 23%. Aperture size and percent open area can be varied for each zone 20. For example, apertures can be from about 2 mm2 to about 5 mm2 and the percent open area can be from about 10% to about 50%.

Apertures 24 can serve the beneficial purpose of providing an open passageway for more viscous fluids or fluids having a solid particle content that do not absorb by ordinary capillarity principles. For example, menses is both relatively viscous (compared to urine or water) and contains a significant amount of solid components, as well as clumped, stringy, or otherwise difficult to absorb fluid components. Such components, as well as the less viscous components of menses can easily and quickly have access to the absorbent core 18 of the absorbent article 10 by passing through apertures 24.

In the embodiment shown in FIG. 2, apertures 24 can serve the additional benefit of capturing fluid and fluid components that would otherwise tend to run off of the absorbent articles 10 and possibly soil the garments of the wearer. For example, if fluid were to run off toward the longitudinal end of the absorbent articles 10 shown in FIG. 2, the portion of apertures 24 could intercept the fluid as it progressed, permitting a relatively unobstructed passage to an underlying absorbent core.

In one embodiment, the topsheet can have a plurality of portions 20 in which the portions 20 differ in percent open area, and/or the plurality of apertures 24 of each respective portion differ in area size. For example, a device 10 can have a central portion 20 as shown in FIG. 1 can have relatively small apertures, for example having an area of from 1 mm$^2$ to about 3 mm$^2$, and a longitudinally-displaced portion 20 as shown in FIG. 2 having relatively large apertures, for example having an area from about 2 mm$^2$ to about 5 mm$^2$. The area size of apertures 24 can be varied, either randomly, or in a gradual gradient from one portion of the device to another. Area size can be varied with respect to device location by varying the length of the melt bond sites and/or amount of stretch in ring rolling when apertures are produced by the method as disclosed in U.S. Pat. No. 5,628,097 issued May 13, 1997 to Benson et al., or U.S. Pat. No. 5,916,661 issued Jun. 29, 1999 to Benson et al.

The topsheet 14 of a sanitary napkin can have various optional characteristics. For example, the topsheet 14 can have channels embossed or other textured surfaces therein to direct fluid flow. Various visual signals, indicia, or other markings can be added, for example by ink jet printing.

The benefit of the present invention can be optimized by tailoring the open area of the apertures 24 and the percent open area of the portion 20 with respect to the caliper (thickness) of the topsheet to be optimized for a given fluid, e.g., menses. It is believed that it is beneficial to use a hydrophilic absorbent core 18 and to keep the topsheet 14 in sustained intimate contact with the absorbent core 18. In this manner, there is a better likelihood that menses entering apertures 24 pass through and into the core 18, rather than being held in the apertures 24. In general, for a given fluid, topsheet and absorbent core system, it is believed beneficial to increase the percent open area with an increase in thickness (which can be an increase in basis weight). In one embodiment, a nonwoven topsheet having a relatively low caliper of about 1 mm can have a percent open area of about 20% to about 30%. A topsheet having a relatively high caliper of about 3 mm can have a percent open area of about 30% to about 50%.

Figure 3:
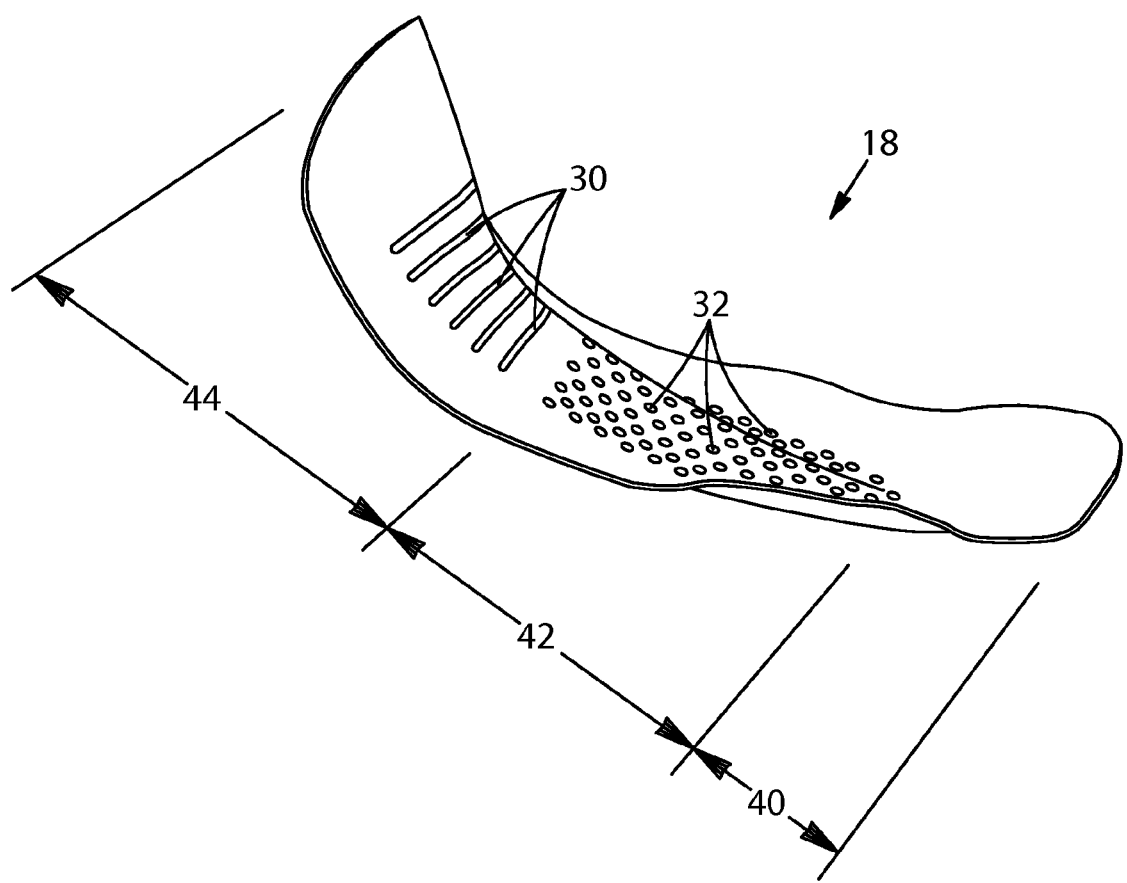
FIG. 3 is a perspective view of an absorbent core of the present invention in an in-use configuration.

Desirable fit of an absorbent article 10 used as a sanitary napkin can be described as having the shape shown in FIG. 3. That is, in use the absorbent article 10 can be cup-shaped in the front, "W" shaped in the middle, and "V" shaped in the back, as well as being generally concave from front to back. This complex shape is difficult to achieve when making and marketing devices such as sanitary napkins in generally flat or flat folded configurations.

Because many elements of an absorbent article 10, such as topsheets or backsheets, are inherently flexible and pliable, improved fit can be best facilitated by providing an absorbent core that is adapted to permit conformable fit when the product is in use. Such an absorbent core can have the features shown in FIG. 4.

An absorbent core can have discrete zones of varying flexibility that act as shaping elements. The zones can be defined by varying patterns of material modification. One material useful for such a core is a soft, absorbent foam, such as polyurethane foam or HIPE foam. The absorbent article 10 may comprise a high capacity and highly absorbent core 18. Absorbent core 18 can be the type generally referred to as HIPE foams, such as those disclosed in U.S. Pat. No. 5,550,167; U.S. Pat. No. 5,387,207; U.S. Pat. Nos. 5,352,711; and 5,331,015. In one embodiment, absorbent core 18 has a capacity after desorption at 30 cm of less than about 10% of its free absorbent capacity; a capillary absorption pressure of from about 3 to about 20 cm; a capillary desorption pressure of from about 8 to about 25 cm; a resistance to compression deflection of from about 5 to about 85% when measured under a confining pressure of 0.74 psi; and a free absorbent capacity of from about 4 to 125 grams/gram. Each of these parameters can be determined as set forth in U.S. Pat. No. 5,550,167. issued Aug. 27, 1996 to DesMarais. The aforementioned properties allow the absorbent core 18 to wick fluid while conforming to the shape of the body. One advantage of utilizing the airlaid or HIPE foam cores as disclosed is that the absorbent core can be made very thin. For example, an absorbent core of the present invention can have an average caliper (thickness) of less than about 3 mm, or less than about 2 mm, and the thickness can be less than about 1 mm. Foams can be more easily modified than conventional absorbent core materials, such as nonwoven batts, airfelt, and coform materials. However, forming apertures or slots as disclosed below can be achieved in foams more easily with known die cutting equipment, including rotary die cutters as disclosed in U.S. Pat. No. 6,702,917, issued Mar. 9, 2004 to Venturino. Such rotary die cutters can be modified to cut slots 30 and cut the absorbent core to shape at the same time.

Figure 4:
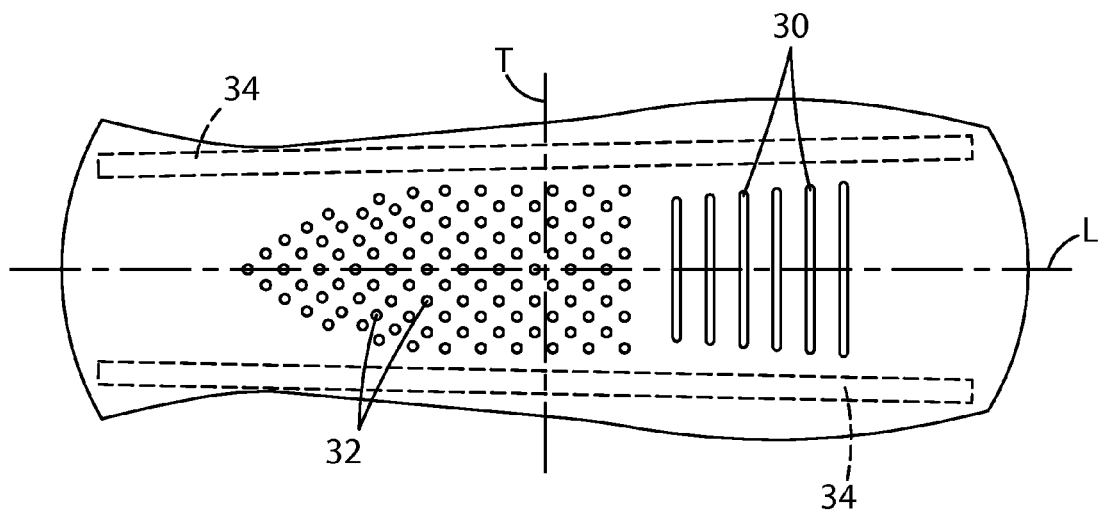
FIGS. 4-6 are plan views showing features of an absorbent core of the present invention.

As shown in FIG. 4, the absorbent core 18 can be asymmetric about a transverse centerline T, and can have a shaping element such as a lateral stiffener 34. Lateral stiffener 34 can increase stiffness along the longitudinal edges of absorbent core 18. Lateral stiffener 34 can be a band or strip from about 10 mm to about 25 mm wide, and generally extend the length of the core 18. By locating the lateral stiffener 34 at the edges of the core 18 it is located in an area that undergoes little width-wise deformation when device 10 is worn, and can transfer compressive forces applied by the legs to other areas of the device where cupping or bending is desired. Lateral stiffeners 34 can comprise adhesive applied to the absorbent core or additional relative stiff materials joined to the absorbent core. If adhesive is used for lateral stiffener 34, the adhesive can also adhere the absorbent core 18 to backsheet 16.

The absorbent core 18 can have a plurality of laterally-oriented slots 30 having an average gap width of at least about 1 mm prior to use. Slots 30 are considered laterally oriented if they have a major vector component at the longitudinal centerline L that is perpendicular to the longitudinal centerline. Thus, as shown in FIG. 4, slots 30 can be substantially parallel, generally linear slots that are each parallel to centerline L, and, therefore, have no vector component in the longitudinal direction. Slots 30 can have other configurations, including generally curved orientations such as those shown in FIGS. 5 and 6. Absorbent core can have additional modifications and features to facilitate desired bending and folding. For example, absorbent core 18 can have additional slits, apertures, perforations, lines of weakness, and the like. In particular, in one embodiment a line of weakness such as perforations or a score line along at least a portion of the longitudinal centerline L can aid in proper formation of a raised hump or ridge along the centerline.

Slots can be completely surrounded by core material. That is, slots can be entirely interiorly disposed, each slot having two ends, such as ends 31 shown in FIG. 6. In general, an imaginary straight line shown as line 33 can connect the ends 31 of slots 30 and align with an edge formed by apertures 32 in a middle zone 42 of core 18. Imaginary line 33 can correlate with an edge of lateral stiffeners 34 so as to aid in lateral compressive formation of a complex three-dimensional shape, as disclosed more fully below.

Figure 5:
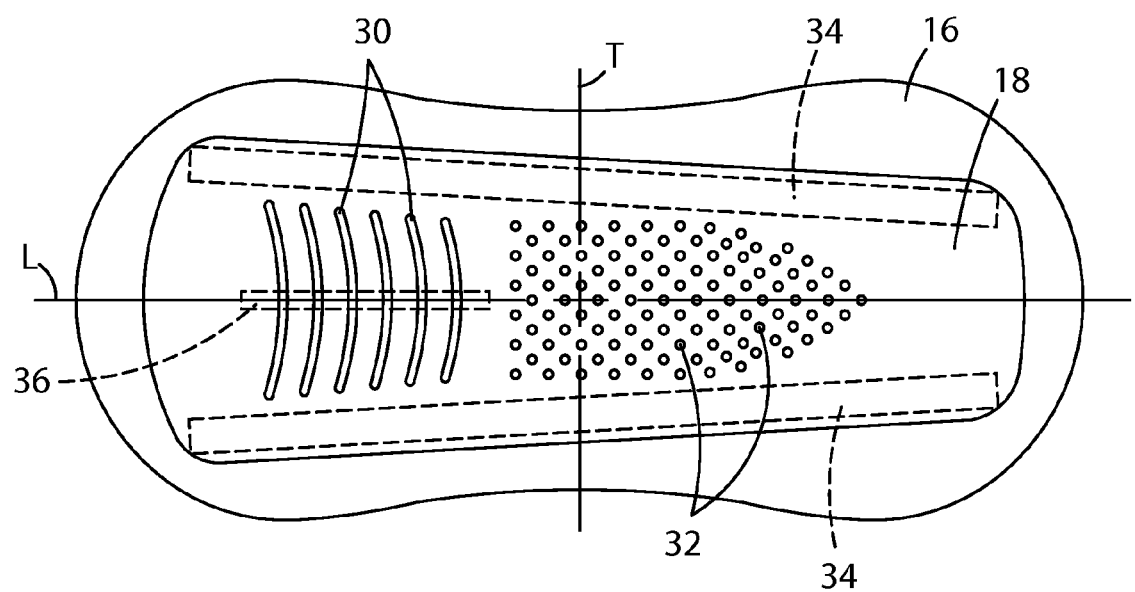
Figure 6:
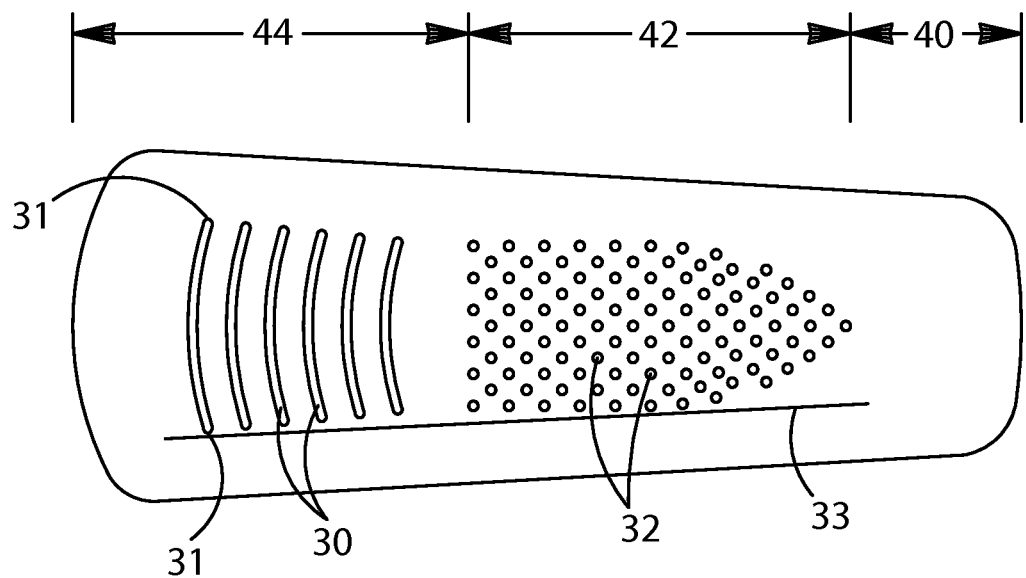

FIG. 5, which shows a sanitary napkin having the topsheet removed so as to see the absorbent core 18 positioned over backsheet 16 of a sanitary napkin having a generally hourglass shape. FIG. 6 shows the absorbent core alone and shows the three zones of the absorbent core can be identified. A first zone 40 at the front of the core 18, which is the narrowest end of an asymmetric core can have only the lateral stiffeners and cup into a concave form when worn. A middle zone 42 can comprise apertures 32 that can both help fluid acquisition as well as reduce stiffness in the middle zone. Stiffness can be reduced as required or desired by making more or fewer apertures, or by varying the size and area density of the apertures 32. A third zone 44 at the rear of the core 18, which is intended to be the back of the device 10 when worn, can have the slots 30.

Slots 30 provide for a reduction in bending resistance when the absorbent article 10 is bent as shown in FIG. 3. That is, when the device is worn, and the rear portion including the third zone of the core 18 is bent about the wearer's buttocks, including the gluteal groove, the absorbent article 10 can bend accordingly due to the slots 30 which allow compression of the core in this area. Thus, as the absorbent article 10 bends in a concave form about the wearers anatomy, the absorbent core 18 can bend and conform accordingly due to the lack of material where material has been removed for slots 30, permitting compression about that area. This allows the material to also conform to the shape of the labia.

Compression of slots 30 in bending accomplishes both ease of bending about the wearer's anatomy for better fit and comfort, and ease of bending into a substantially inverted "V" shape to fit into the gluteal groove of the wearer, thereby minimizing fluid runoff from the body in this region. Therefore, both longitudinal folding is accomplished in multiple axes, aiding in both fit and fluid handling advantages. It has been found that slots spaced so as to provide compression along about 12 mm of the longitudinal axis in the rear portion of the absorbent article 10 can be sufficient for the fit and fluid protection benefit. In one embodiment, 6 slots spaced about 10 mm apart and having a width of about 2 mm was found sufficient.

The absorbent core 18 can permit the absorbent article 10 to be produced as a two-dimensional, flat device for packaging, and yet to achieve a complex three dimensional shape when used by the wearer. To aid in taking the complex three dimensional shape, absorbent core 18 can include an elastic member 36. Elastic member 36 can be a strand of elastic material that is attached or joined to core 18 at least at two ends thereof. Elastic member 36 can provide for 15 mm to 50 mm of contraction with a contractive force of about 40 grams to about 100 grams. In one embodiment, elastic member can provide for 20 mm to 30 mm of contraction, and the contractive force can be 50 grams to 60 grams. Elastic member can be Stretchrite® soft stretch elastic 3 mm wide (about 0.125 inch) available from Rhode Island Textile Co. of Pawtucket R.I. When packaged in a general flat condition, elastic 36 can be in a stretched position. Upon removing from the package and/or when worn, elastic 36 can contract, causing the third zone to compress in the region of slots 30. The contraction of an elastic strip or strand 36 aligned along longitudinal centerline L, as shown in FIG. 5, tends to draw the absorbent core into a more defined and stable inverted V-shape in the rear portion of the absorbent article 10.

Apertured film materials suitable for use as the topsheet include those apertured plastic films that are non-absorbent and pervious to body exudates and provide for minimal or no flow back of fluids through the topsheet. Nonlimiting examples of other suitable formed films, including apertured and non-apertured formed films, are more fully described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,324,314, issued to Radel et al. on Aug. 3, 1982; U.S. Pat. No. 4,463,045, issued to Ahr et al. on Jul. 31, 1984; U.S. Pat. No. 5,006,394, issued to Baird on Apr. 9, 1991; U.S. Pat. No. 4,609,518, issued to Curro et al. on Sep. 2, 1986; and U.S. Pat. No. 4,629,643, issued to Curro et al. on Dec. 16, 1986. Commercially available formed filmed topsheets include those topsheet materials marketed by the Procter&Gamble Company (Cincinnati, Ohio) under the DRI-WEAVE® tradename.

Nonlimiting examples of woven and nonwoven materials suitable for use as the topsheet include fibrous materials made from natural fibers, modified natural fibers, synthetic fibers, or combinations thereof. These fibrous materials can be either hydrophilic or hydrophobic, but it is preferable that the topsheet be hydrophobic or rendered hydrophobic. As an option portions of the topsheet can be rendered hydrophilic, by the use of any known method for making topsheets containing hydrophilic components. One such method include treating an apertured film component of a nonwoven/apertured thermoplastic formed film topsheet with a surfactant as described in U.S. Pat. No. 4,950,264, issued to Osborn on Aug. 21, 1990. Other suitable methods describing a process for treating the topsheet with a surfactant are disclosed in U.S. Pat. Nos. 4,988,344 and 4,988,345, both issued to Reising et al. on Jan. 29, 1991. The topsheet can comprise hydrophilic fibers, hydrophobic fibers, or combinations thereof.

When the topsheet comprises a nonwoven fibrous material in the form of a nonwoven web, the nonwoven web may be produced by any known procedure for making nonwoven webs, nonlimiting examples of which include spunbonding, carding, wet-laid, air-laid, meltblown, needle-punching, mechanical entangling, thermo-mechanical entangling, and hydroentangling. Other suitable nonwoven materials include low basis weight nonwovens, that is, nonwovens having a basis weight of from about 18 g/m$^2$ to about 25 g/m$^2$. An example of such a nonwoven material is commercially available under the tradename P-8 from Veratec, Incorporation, a division of the International Paper Company located in Walpole, Mass.

The backsheet can be any known or otherwise effective backsheet material, provided that the backsheet prevents external leakage of exudates absorbed and contained in the absorbent article. Flexible materials suitable for use as the backsheet include, but are not limited to, woven and nonwoven materials, laminated tissue, polymeric films such as thermoplastic films of polyethylene and/or polypropylene, composite materials such as a film-coated nonwoven material, or combinations thereof.

The absorbent core is typically positioned between the topsheet and the backsheet. As used herein, the term "absorbent core" refers to a material or combination of materials suitable for absorbing, distributing, and storing aqueous fluids such as urine, blood, menses, and water found in body exudates. The size and shape of the absorbent core can be altered to meet absorbent capacity requirements, and to provide comfort to the wearer/user.

The absorbent core may exhibit a 30 minute Vertical Wicking Height of at least about 12 cm. The absorbent core will comprise absorbent foam material which may exhibit a 60-minute Vertical Wicking Height of at least about 15 cm. Vertical wicking, i.e., fluid wicking in a direction opposite from gravitational force, is an especially desirable performance attribute for absorbent structures herein. These structures are utilized in absorbent articles in a manner such that fluid to be absorbed must be moved within the article from a relatively lower position to a relatively higher position within the absorbent core of the article and horizontally in the plane. Accordingly, the ability of these absorbent structures to wick fluid against gravitational forces is particularly relevant to their functioning as absorbent materials in the present absorbent articles.

Vertical wicking effectiveness for absorbent structures useful herein can be measured and quantified in a number of ways, but one typical indicator of vertical wicking performance is the height to which a vertically positioned test strip of absorbent material will wick synthetic urine (0.9% saline solution) from a reservoir within a specified period of time. For purposes of the present invention, this height, termed the Vertical Wicking Height, is determined by the procedure described in the U.S. Pat. No. 5,147,345 issued to Young et al. on Sep. 15, 1992, which description is incorporated herein by reference.

The absorbent articles can also include a suitable lotion composition in any suitable amount. Generally, a safe and effective amount of the lotion composition is applied to an absorbent article described herein wherein such safe and effective amounts include applying from about 0.0015 mg/cm2 (0.01 mg/in$^2$) to about 100.5 mg/cm2 (648 mg/in$^2$), preferably from about 0.003 mg/cm2 (0.02 mg/in$^2$) to about 12.4 mg/cm2 (80 mg/in$^2$), more preferably from about 0.02 mg/cm2 (0.015 mg/in$^2$) to about 7.75 mg/cm2 (50 mg/in$^2$), of the lotion composition to the absorbent article.

Processes for assembling absorbent articles such as the disposable absorbent articles described herein include conventional techniques known in the art for constructing and configuring disposable absorbent articles. For example, the backsheet and/or the topsheet can be joined to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031.

Figure 7:
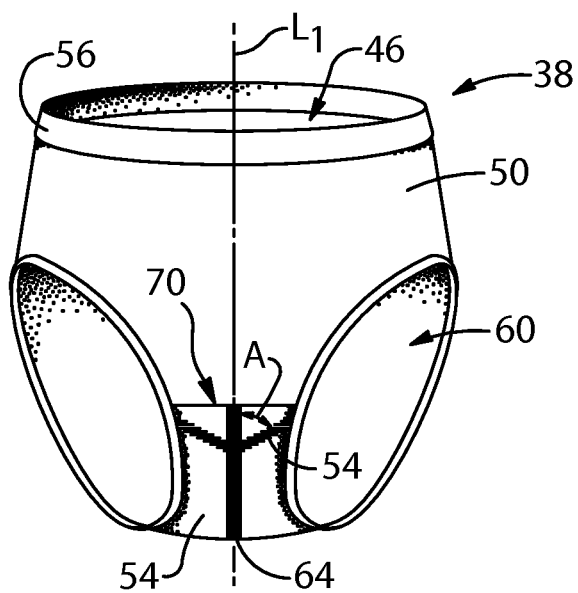
FIG. 7 is a front view of a preferred embodiment of a menstrual pant or panty for use with the absorbent article of the present invention.
Figure 8:
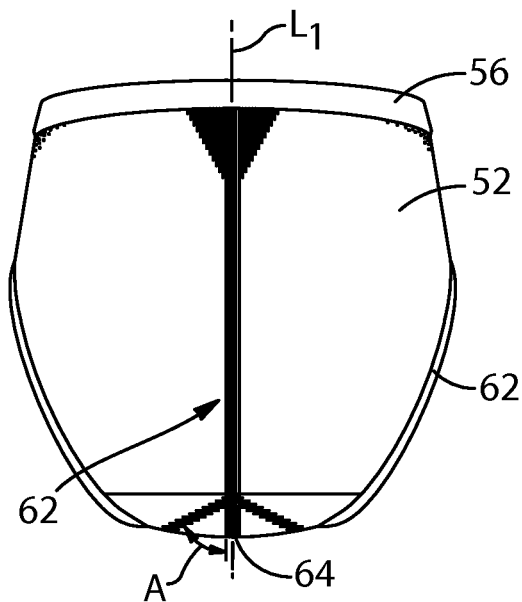
FIG. 8 is a rear view of a preferred embodiment of a menstrual pant or panty for use with the absorbent article of the present invention.

FIGS. 7 and 8 show front and rear views of a supporting garment in the form of a menstrual pant or panty 38. As is shown in FIGS. 7 and 8, the menstrual pant or panty 38 comprises a front portion 50 which may be in the form of a front panel, a rear portion 52 which may be in the form of a rear panel, a crotch region or portion 54 which may be in the form of a crotch panel, a pair of leg openings 60 which may be elasticized, and an elasticized waistband 56. The menstrual pant or panty 38 is also provided with a waist opening 46 allowing entry into the menstrual pant or panty 38. The menstrual pant or panty 38 further comprises an extensible lifting member such as lifting strip 62 disposed along the longitudinal centerline 'L1 in the rear portion 52, and a longitudinal stretch control member 64 disposed along the longitudinal centerline in the crotch portion 54. It should be noted that any seam or gusset 70 at the front end of the crotch portion 54 is preferably situated so that it lies under or behind (that is, rearward of) the pubic bone so that the pubic bone does not interfere with the fit of the menstrual pant or panty. It should also be understood that any or all of the features of the menstrual pant or panty 38 described herein may be knit into the menstrual pant or panty, and need not comprise sewn together portions of the menstrual pant or panty.

The extensible lifting member or lifting strip 62 may comprise of an elastomeric material. The elastomeric material may comprise one or more elastic strands, elastomeric films, elastomeric ribbons, elastomeric nonwovens, elastomeric filaments, elastomeric adhesives, elastomeric foams, scrims or combinations thereof.

The absorbent article 10 can be utilized by placing the absorbent article 10 in the crotch portion of the menstrual pant or panty 38. The absorbent article 10 is placed in the crotch 54 portion of the menstrual pant or panty with one end extending toward the front section of the menstrual pant or panty and the other end towards the back section of the menstrual pant or panty. The absorbent article 10 may extend to cover from the mons pubis to the anus. The backsheet 16 is placed in contact with the inner surface of the center of the crotch portion 54 of the menstrual pant or panty. The absorbent article can include hair like projections 74 such as those described in U.S. Pat. No. 8,083,725 in US issued Dec. 27, 2011 to Bonelli et al., herein incorporated by reference. The hair-like projections 74 of the mechanical fastening material 76 on the garment-facing side 78 of the absorbent article engage with the knit material from which the crotch portion 54 of the menstrual pant or panty 38 is made. The wearer then pulls on the menstrual pant or panty 38.

The menstrual pant or panty 38 may have indicative marks to determine appropriate pad placement. These marks may be print signals on the menstrual pant or panty and/or absorbent article to properly place the absorbent article, the use of physical aspects of the absorbent article, such as, for example, the center of a wing, to place the article, physical characteristics of the menstrual pant or panty, such as, for example, a tag, stitching, a color change, and/or the use of a relationship between print signal on the absorbent article and the physical characteristics of the absorbent article to place the absorbent article.

Figure 9:
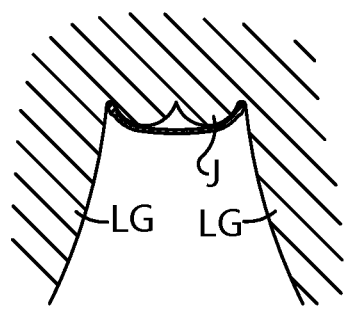
FIG. 9 is a cross-sectional view taken transversely through a portion of a wearer's body which shows how a prior art conventional pair of panties often fit when the wearer's legs are apart.
Figure 10:
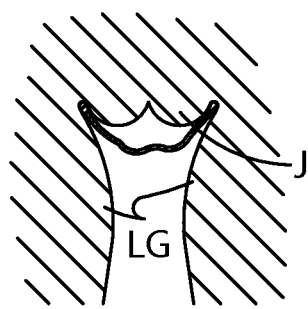
FIG. 10 is a cross-sectional view taken transversely through a portion of a wearer's body which shows how a prior art conventional pair of panties often fit when the wearer's legs are together.

FIGS. 9 and 10, respectively, show examples of how a conventional prior art pair of panties fits in the crotch region when the wearer's legs, LG, are apart, and when they are brought together. As shown in FIG. 9, when the wearer's legs are apart, the crotch region of a conventional pair of panties "gaps" along a longitudinally oriented area centered about the space between the wearer's labia (which are designated by reference letter J). As shown in FIG. 10, the crotch region of these conventional panties sag when the wearer's legs are brought together.

Figure 11:
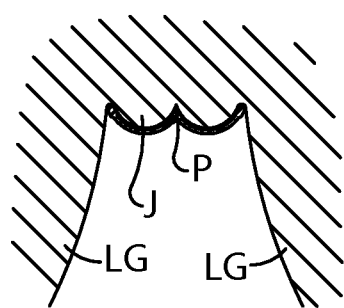
FIG. 11 is a cross-sectional view taken transversely through a portion of a wearer's body which provides one example of how the menstrual pant or panty used with the absorbent article of the present invention fits when the wearer's legs are apart.
Figure 12:
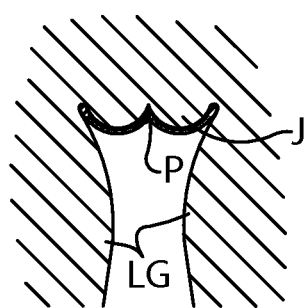
FIG. 12 is a cross-sectional view taken transversely through a portion of a wearer's body which provides an example of how the menstrual pant or panty used with the absorbent article of the present invention fits when the wearer's legs are together.

The menstrual pant or panty as shown schematically in FIGS. 11 and 12, on the other hand, comfortably fits against and conforms to the inside and outside surfaces of the labia majora whether the wearer's legs are apart, or together. The menstrual pant or panty maintains the coverage of the desired areas of the wearer's body without applying significant "girdlelike" forces. As shown in FIGS. 11 and 12, in cross-section, the menstrual pant or panty preferably maintains a modified cusp shaped configuration in this area throughout a range of body motions (that is, dynamically). The cross sectional configuration of the menstrual pant or panty is described as being a "modified" cusp-shape because it may, but preferably does not form a point, P, where the curved portions of the cusp-like shape meet in the longitudinally oriented area in the space between the wearer's labia, but is more rounded, and preferably convex in this area.

The menstrual pant or panty fits against the wearer's body so closely, particularly in the crotch region, that it is like a comfortable "second skin". The absorbent article 10 preferably does not alter or override the tendency of the menstrual pant or panty to achieve this "second skin" fit. The absorbent article 10 is preferably sufficiently flexible so that it assumes a configuration similar to the crotch region of the menstrual pant or panty. Preferably, the absorbent article 10 also conforms to the shape of the wearer's pudendal region in use. In certain embodiments, the absorbent article conforms to the shape of the wearer's pudendal region regardless of whether the wearer's legs are together or apart.

The absorbent article 10 can flex under the forces applied by the menstrual pant or panty 38 that are used to hold the absorbent article comfortably against the wearer's body. If the absorbent article flexes under these forces, it will not override the tendency of the menstrual pant or panty to achieve the desired fit, and the absorbent article 10 will assume a shape similar to the crotch region of the menstrual pant or panty 38. The menstrual pant or panty 38 described herein preferably applies body-contacting pressures to the wearer's body longitudinally through the crotch of 25 to 100 g/cm². The menstrual pant or panty 38 described herein preferably applies body-contacting pressures to the wearer's body of greater than about 25 g/cm², greater than about 30 g/cm², greater than about 35 g/cm², greater than about 40 g/cm², greater than about 45 g/cm², or greater than about 50 g/cm². Alternatively, the menstrual pant or panty 38 described herein preferably applies body-contacting pressures to the wearer's body of less than about 100 g/cm², less than about 95 g/cm², less than about 90 g/cm², less than about 85 g/cm², less than about 80 g/cm², less than about 75 g/cm², less than about 70 g/cm², less than about 65 g/cm², or less than about 60 g/cm².

The menstrual pant or panty 38 that is used to hold the absorbent article comfortably against the wearer's body also may exhibit a total waist to hip force of between about 200 g/cm to about 2000 g/cm, about 200 g/cm to about 1200 g/cm, about 200 g/cm to about 900 g/cm, about 200 g/cm to about 600 g/cm, about 300 g/cm to about 800 g/cm, about 300 g/cm to about 700 g/cm, about 300 g/cm to about 600 g/cm, about 300 g/cm to about 500 g/cm, or about 300 g/cm to about 400 g/cm. Without being bound to any theory, it is believed that using lighter weight absorbent articles allows one to reduce the waist to hip ratio while still keeping the absorbent article in close conforming contact to the body. Traditional marketed menstrual pants may exhibit total waist to hip forces greater than standard undergarments not designed to be worn as menstrual pants. These increased waist to hip force may range between 650 g/cm to 900 g/cm.

TABLE 1

|  | target hip circumference (cm) | corresponding target circumferential force (gf/cm) |
|---|---|---|
| Marketed Menstrual Pant A | 92 | 712 |
|  | 100 | 891 |
| Marketed Menstrual Pant B | 92 | 663 |
|  | 100 | 817 |

The menstrual pant or panty 38 may have a shorter longitudinal length pass through the center of the crotch that generates a vertical lifting force into the crotch area to hold the absorbent article securely against the body. The center longitudinal length pass member may be between 0.5% to 20%, 1% to 15%, or 1% to 10% shorter than the overall panty pitch. The longitudinal length pass member may have a modulus of between 1 to 10 times, 3 to 7 times, or 2 to 8 times stiffer then the surrounding panty material. The center longitudinal length pass member may have a modulus between about 10 g/cm² to about 40 g/cm², about 15 g/cm² to about 35 g/cm², or about 20 g/cm² to about 30 g/cm².

The absorbent article 10 and menstrual pant or panty 38 also differ from prior sanitary napkins and conventional underwear in the sustained nature of the contact of the absorbent article with the wearer's body. Some current sanitary napkins may occasionally assume a "W"-shaped cross sectional configuration during wear, such as when the wearer is sitting. However, conventional underwear does not provide a constant force against the wearer's body to hold the sanitary napkin in place under all circumstances, such as when the wearer is walking or standing, or when the wearer's legs are apart. The absorbent article 10 and the menstrual pant or panty 38, on the other hand, provide such sustained contact with the wearer's body. The absorbent article may be described as being substantially maintained in sustained contact with the wearer's body, in which case the absorbent article need not be in complete and/or continuous contact with the wearer's body, but is maintained in contact with the wearer's body more than it is out of contact with the wearer's body.

Applicants have discovered that using the absorbent article 10 and menstrual pant or panty 38 described herein, also allows for a more comfortable fit around the waist while providing the constant force needed to maintain contact with the wearer's body. This is unlike traditional menstrual pants that compensate for the weight of the absorbent article by increasing the waist to hip force outside of the range of traditional undergarments. These increased waist to hip force used by menstrual pants may cause discomfort and markings to the body while providing the necessary force to keep the larger absorbent article close to the body. Applicants have found that using the absorbent article described herein allows one to reduce the waist to hip force to levels found in traditional undergarments.

The absorbent article 10 can be capable of maintaining contact with and covering at least a portion of the inside surfaces of the wearer's labia, the exterior surfaces of the wearer's labia, and the menstrual pant or panty 38. The absorbent article 10 preferably covers an area centered about the wearer's labia having projected width of at least about 1 inch (about 2.5 cm). The absorbent article may cover substantially all of the interior surfaces of the wearer's labia up to and including contacting and covering the floor of the wearer's vestibule. The absorbent article may also cover substantially all of the exterior surfaces of the wearer's labia.

Another way of describing the configuration the absorbent article 10 may take during wear is by looking at the different regions of the absorbent article 10. The absorbent article 10 preferably has a longitudinal central region centered about its longitudinal centerline, L, that is capable of being positioned in the space between the wearer's labia. This longitudinal central region may be of any suitable width that is less than the width of the entire absorbent article. The longitudinal central region may extend the full length of the absorbent article 10, or less than the full length of the absorbent article. The longitudinal central region preferably has at least a portion (typically along the longitudinal centerline of the absorbent article) that is capable of residing in the space between the wearer's labia at an elevation that is higher (when the wearer is standing) than at least some portions of the absorbent article 10 that are located laterally outboard of the longitudinal central region. The absorbent article 10 is preferably capable of assuming such a configuration without compression by the inner portions of the wearer's thighs.

The absorbent article 10 can cup the labia from front to back. The absorbent article may cover the wearer's clitoris, but preferably does not extend substantially forward beyond the wearer's mons pubis. The absorbent article may extend to the anus. The absorbent article 10 may be spaced slightly away from the clitoris, or it may fit closely against the clitoris, as it does relative to the other regions of the wearer's body.

The absorbent article 10 can be made somewhat larger if the edge portions thereof which may be contacted by the inside surfaces of the wearer's thighs, LG, do not translate forces acting thereon to the remainder of the absorbent article so as to cause the absorbent article to bend or crumple, and/or shift from the desired position under the wearer's vaginal introitus. For example, it is also contemplated herein that an absorbent article 10 can be constructed which has the desired flexibility, fit, and an absorbent region with the preferred small size described herein (e.g., covering the pudendal region and the perineum), but which has regions that are located outboard of these regions which merely serve a "drop cloth" function, which have minimal or no absorbency. For instance, such regions could be comprised only of topsheet and backsheet materials, and possibly a thin layer of absorbent material therebetween. It is considered that such an embodiment will also fall within the scope of the present invention.

Test Methods Section
Stretch Modulus Test
This method quantifies a stretch modulus of the extensible materials that may be used in an undergarment over an extension range similar to that seen in the wear cycle of an undergarment.
The method described in INDA (Association of Nonwoven Fabric Industry) Standard Test 110.1-92 is suitable.

A commercial tensile testing from Instron Engineering Corp., Canton, Mass. Or SINTECH-MTS Corporation, Eden Prairie, Minn. (or a comparable tensile tester) is used for this test. The instrument is interfaced with a computer for controlling the test speed and other test parameters, and for collecting, calculating and reporting the data. The stretch modulus is measured under typical laboratory conditions (i.e., room temperature of about 20° C. and relative humidity of about 50%). The procedure for determining the stretch modulus involves the following steps:

1. choose the appropriate jaws and load cell for the test; the jaws are wide enough to fit the sample, typically 2.54 cm (1 inch) wide jaws are used: the load cell is chosen so that the tensile response from the sample tested will be between 25% and 75% of the capacity of the load cells or the load range used. Typically a 50N load cell is used.
2 calibrate the tester according to the manufacturer's instructions.
3 set the gauge length at 6 cm and the sample width to 1 cm
4 place the sample in the flat surface of the jaws such that the longitudinal axis of the sample is substantially parallel to the gauge length direction.
5 pull the sample to 75% strain at a cross head speed of 254 mm/min From the data collected in step 5, the stretch modulus is determined by the linearized slope of the force versus strain curve between 75% strain and 25% strain.

Body Contact Force Test
This method determines the force exerted on a wearer's body by an elasticized undergarment. A commercially available mannequin is used to minimize error due to body dimension variation.

Apparatus
Mannequin Suitable is a female, anatomically correct mannequin as is used to train medical personnel in catherization techniques. The mannequin has the following dimensions: thigh circumference-54 cm, waist circumference-92 cm, hip circumference-95 cm, and front waist to back waist through groin-59 cm and is available from NASCO of Ft. Atkinson, Wis. as catalog number LF 856.
Pressure Sensors Ultra thin pizeo resistive pressure sensors (5 mm×15 mm, 0-10 mm Hg pressure range, with biomedical lead wires) as are available from Vistamedical, Ltd. of Winnipeg, Manitoba, Canada.
Computer Pentium based computer with 8 MB RAM using the Windows 95t operating system. A laptop computer as is available from Dell Computer Corp. of Austin, Tex. as a model Latitude LM is suitable.
Electronic Interface Module Model
FSA-C-2-1.00 as is available from Vistamedical, Ltd. of Winnipeg, Manitoba, Canada.
Data Acquisition Software
FSA Version 3.1 as is available from Vistamedical, Ltd. of Winnipeg, Manitoba, Canada.
Method
1. Attach the leads from each sensor to the interface module according to the manufacturer's instructions. Calibrate each sensor by placing the sensor on an inflated air bladder (7.5 g/cm$^2$) and subjecting the sensor to known pressures (up to 7.5 g/cm$^2$) provided by a second air bladder that is disposed on the first bladder, the bladders being confined within a containment box as is supplied by the manufacturer. The FSA software acquires the signal produced and compares the signal with the calibration pressure which is entered by the operator. This comparison is used to build a calibration table which is stored as a file in the computer.

2. Attach the sensors to the mannequin using double sided transfer tape (available from 3M of St. Paul, Minn. as part no. 950). A first pair of sensors is placed on the apex of the mannequin's labia minora centered on the mannequin's urethra. A second pair of sensors is placed on the apex of the mannequin's labia majora at a position 6 mm anterior to sensors. A third pair of sensors is placed on the surface of the mannequin's gluteus at a position 32 mm posterior to the mannequin's posterior commissure of the labia minora. The fourth and last set of sensors is placed on the surface of the mannequin's mons at a position 65 mm anterior to the center of the mannequin's urethra.

3. Pull the garment on to the mannequin so it is smooth and symmetrically disposed about the mannequin's coronal centerline. The garment should be drawn up so as to be moderately tight. Reproducibility can be improved by recording the pressures at the sensors positioned on the surface of the mannequin's gluteus at a position 32 mm posterior to the mannequin's posterior commissure of the labia minora and the sensors on the surface of the mannequin's mons at a position 65 mm anterior to the center of the mannequin's urethra. Record the pressures for a first garment position subsequent garments so as to have as close to the same pressure as possible at these sensors.

4. Acquire force data from the remaining sensors using the interface module and software according to the manufacturer's instructions. A minimum of 4 samples should be evaluated. If desired, the acquired data can be exported into a spreadsheet file for further analysis by following instructions provided with the software.

5. Report mean and standard deviation for each sample. When samples are being compared, known statistical techniques (e.g. Analysis of Variance) can be used.

Longitudinally Shorter Path Length Test

This test determines the longitudinal path length of the relaxed extensible lifting member relative to the relaxed longitudinal length of the panty. A shorter path length coupled with a higher stretch modulus facilitates conformity through the crotch.

Method

1. Cut the extensible lifting member out from the panty.
2. Cut off the leg elastics from the panty.
3. Cut the remaining panty at both leg openings, longitudinally up to the waist opening such that the panty can be laid open achieving an appearance similar to that of an un-applied taped diaper.
4. Lay the panty flat such that the top of the front waist and top of the back waist are now separated longitudinally.
5. Lay the cut out extensible lifting member into the opening left from its having been removed, such that any difference in longitudinal length between the member and the cut out opening are reflected at the back waist of the panty.
6. Measure the length longitudinally from the front waist to the back waist.
7. Measure the length longitudinally from the front waist to the end of the extensible lifting member that lies closest to the back waist.
8. The percent reduction from the measurement taken in step 7 to that taken in step 6 is the path length reduction enabled by the extensible lifting member.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A system comprising:
    a. menstrual pant, said menstrual pant comprising:
        i. A front part;
        ii. A back part;
        iii. A crotch part provided so as to bridge between the front part and the back part, the crotch being utilized for fitting a sanitary napkin,
        iv. A waist opening part provided in an upper edge of the front part and an upper edge of the back part
        v. A pair of leg openings provided below both side edges of the front part and both side edges of the back part; and
        vi. a lifting strip disposed along the longitudinal centerline in the rear portion, wherein the menstrual pant applies body-contacting pressures to the wearer's body longitudinally through the crotch of 25 to 100 g/cm$^2$;
    b. an absorbent article comprising an a topsheet having a body facing surface, a backsheet joined to said topsheet; and an absorbent core disposed between said topsheet, wherein the absorbent article exhibits a 30-minute Vertical Wicking Height of at least about 12 cm, wherein the absorbent article has a longitudinal central region that is capable of being positioned in the space between the wearer's labia, said longitudinal central region being capable of residing in said space between the wearer's labia at an elevation that is higher than at least some portions of the absorbent article that are located laterally outboard of said longitudinal central region and wherein the absorbent article is capable of assuming such a configuration without compression by the inner portion of a wearer's thighs.

2. The absorbent article of claim 1, wherein said absorbent core is asymmetric about a transverse centerline.

3. The absorbent article of claim 1, wherein said absorbent core comprises a HIPE foam.

4. The absorbent article of claim 1, wherein the absorbent article exhibits a 60 minute Vertical Wicking Height of at least about 15 cm.

5. The absorbent article of claim 1, wherein portions of said absorbent article outside said longitudinal central region are capable of cupping the wearer's labia from the front of the labia to the back of the labia.

6. The menstrual pant of claim 1, wherein the lifting strip applies a body contacting pressure to the wearer's body longitudinally through the crotch of 25 to 70 g/cm$^2$.

7. An absorbent article according to claim 1, wherein the absorbent article has a cup-shaped configuration prior to use.

8. The absorbent article of claim 1, wherein the absorbent article comprises one or more slots, wherein said slots have an average width of at least about 1 mm.

9. An absorbent article according to claim 1, wherein the absorbent article is capable of covering substantially all of the interior surfaces of the wearer's labia up to and including the floor of the wearer's vestibule.

10. An absorbent article according to claim 1, wherein the absorbent article is capable of covering substantially all of the exterior surfaces of the wearer's labia.

11. The menstrual pant of claim 1, wherein the menstrual pant further comprises a total waist to hip force of between 200 g/cm to 2000 g/cm.

12. The menstrual pant of claim 1, wherein the menstrual pant further comprises a total waist to hip force of between 300 g/cm to 700 g/cm.

13. A menstrual pant, said menstrual pant comprising:
   a. A front part;
   b. A back part;
   c. A crotch part provided so as to bridge between the front part and the back part, the crotch being utilized for fitting a sanitary napkin,
   d. A waist opening part provided in an upper edge of the front part and an upper edge of the back part
   e. A pair of leg openings provided below both side edges of the front part and both side edges of the back part; and
   f. a lifting strip disposed along the longitudinal centerline in the rear portion, wherein the lifting strip applies a body-contacting pressure to the wearer's body longitudinally through the crotch of 25 to 100 g/cm², wherein the lifting strip comprises a longitudinal length pass member, wherein the longitudinal length pass member is between about 0.5% to about 20% shorter than an overall pitch of the menstrual pant.

14. The menstrual pant of claim 13, wherein the lifting strip applies a body contacting pressure to the wearer's body longitudinally through the crotch of 25 to 70 g/cm².

15. The menstrual pant of claim 13, wherein the menstrual pant further comprises a total waist to hip force of between 200 g/cm to 2000 g/cm.

16. The menstrual pant of claim 13, wherein the menstrual pant further comprises a total waist to hip force of between 300 g/cm to 700 g/cm.

17. A system comprising:
   a. menstrual pant, said menstrual pant comprising:
      i. A front part;
      ii. A back part;
      iii. A crotch part provided so as to bridge between the front part and the back part, the crotch being utilized for fitting a sanitary napkin,
      iv. A waist opening part provided in an upper edge of the front part and an upper edge of the back part
      v. A pair of leg openings provided below both side edges of the front part and both side edges of the back part; and
      vi. a lifting strip disposed along the longitudinal centerline in the rear portion, wherein the menstrual pant applies body-contacting pressures to the wearer's body longitudinally through the crotch of 25 to 100 g/cm², wherein the menstrual pant lifting strip comprises a longitudinal length, wherein the longitudinal length is between about 0.5% to about 20% shorter than an overall pitch of the menstrual pant;
   b. an absorbent article comprising an a topsheet having a body facing surface, a backsheet joined to said topsheet; and an absorbent core disposed between said topsheet, wherein the absorbent article exhibits a 30-minute Vertical Wicking Height of at least about 12 cm.

18. The absorbent article of claim 17, wherein said absorbent core comprises a HIPE foam.

19. An absorbent article according to claim 17, wherein the absorbent article has a cup-shaped configuration prior to use.

20. An absorbent article according to claim 17, wherein the absorbent article is capable of covering substantially all of the exterior surfaces of the wearer's labia.

21. The menstrual pant of claim 17, wherein the menstrual pant further comprises a total waist to hip force of between 200 g/cm to 2000 g/cm.

\* \* \* \* \*